United States Patent [19]

Makonkawkeyoon

[11] 4,152,242
[45] May 1, 1979

[54] IMMUNODISC ELECTROPHORESIS

[75] Inventor: Sanit Makonkawkeyoon, Chiengmai, Thailand

[73] Assignee: International Foundation of Microbiology, Chicago, Ill.

[21] Appl. No.: 425,089

[22] Filed: Dec. 17, 1973

Related U.S. Application Data

[63] Continuation of Ser. No. 167,367, Jul. 29, 1971, abandoned.

[51] Int. Cl.² .................... G01N 27/26; G01N 27/28
[52] U.S. Cl. .......................... 204/299 R; 204/180 G; 23/230 B; 424/12
[58] Field of Search ............... 204/180 G, 299, 180 R; 23/230 B; 424/12

[56] References Cited

U.S. PATENT DOCUMENTS

| | | | |
|---|---|---|---|
| 3,346,479 | 10/1967 | Natelson | 204/301 |
| 3,499,833 | 3/1970 | Ferris et al. | 204/299 |
| 3,799,863 | 3/1974 | Zeineh | 204/299 |

*Primary Examiner*—Arthur C. Prescott
*Attorney, Agent, or Firm*—John L. Parker

[57] ABSTRACT

An electrophoretic gel apparatus and analytical method are provided for analyzing samples without the need for removing the gel from the apparatus. The electrophoretic gel is provided with a central opening therethrough for accomodating an analytical reagent, so that the latter may react with electrophoretically separated components of a sample undergoing analysis.

6 Claims, 8 Drawing Figures

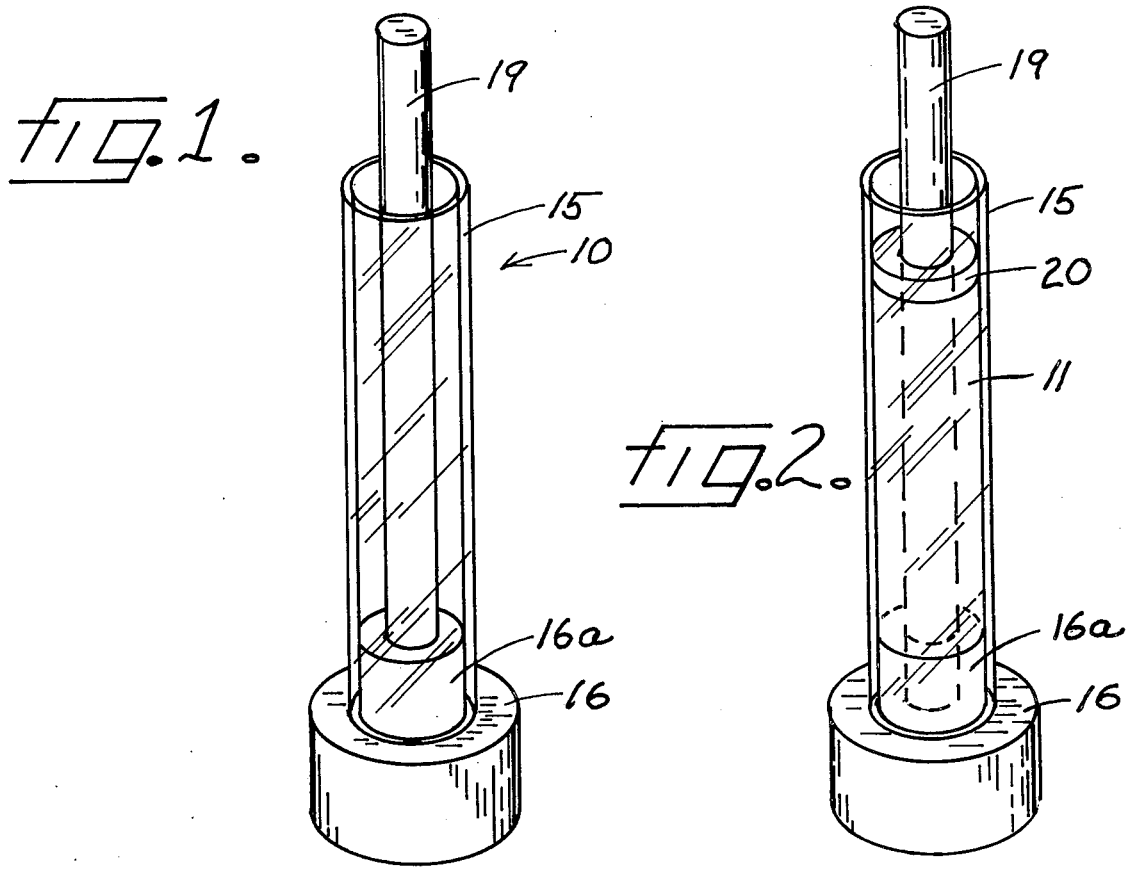
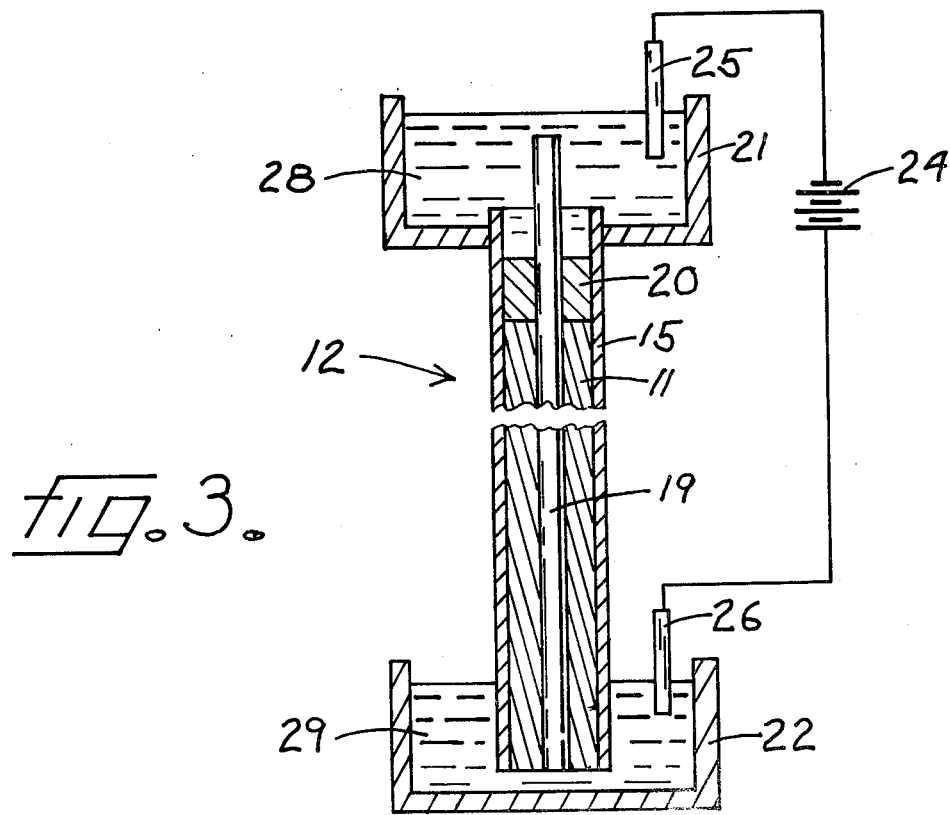

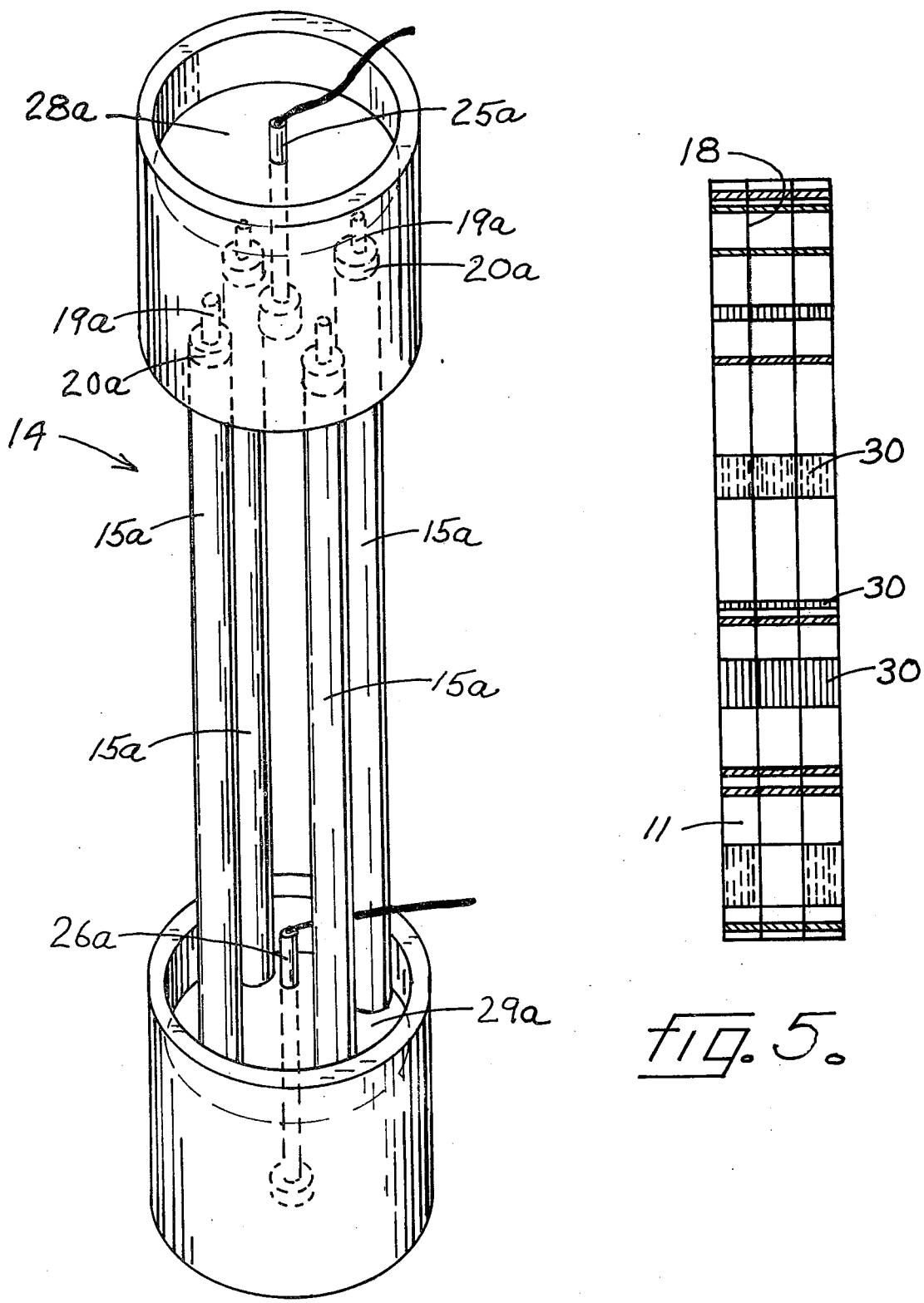

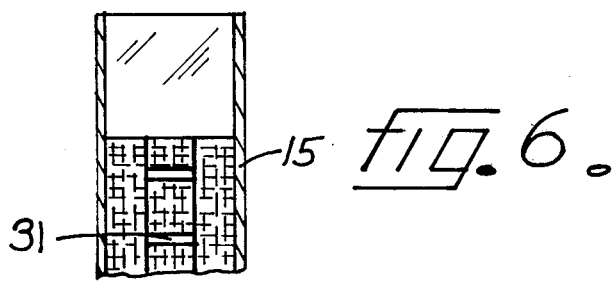
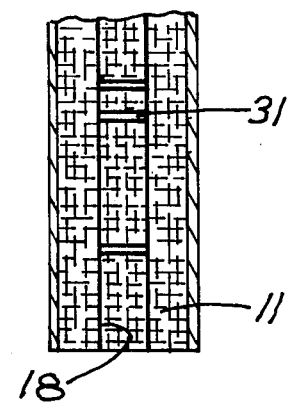
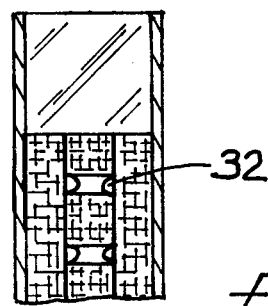
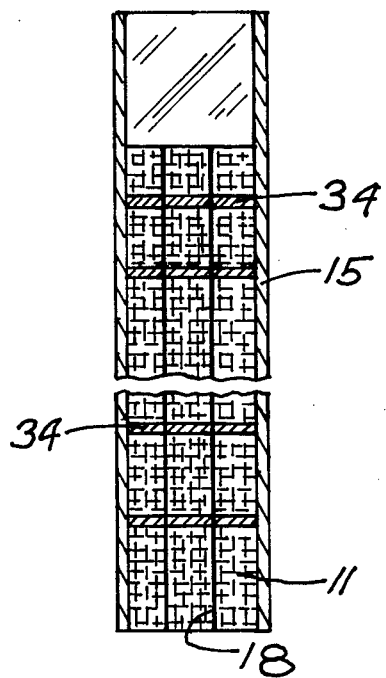

IMMUNODISC ELECTROPHORESIS

DESCRIPTION OF THE INVENTION

This is a continuation of my application Ser. No. 167,367 filed July 29, 1971 now abandoned.

The present invention relates to the detection of antigens, enzymes, and other biologically active and inactive components of biological and other fluid and extracts using electrophoresis techniques. More particularly, the invention is concerned with improvements in disc electrophoresis techniques used in such analytical determinations.

Disc electrophoresis using polyacrylamide and other suitable gels has been used to characterize and resolve complex mixtures of proteins such as serum, tissue extracts, and purified hormones and enzymes. In this technique, a sample containing suspended particles is placed on top of a column of polyacrylamide, starch or other suitable gel capable of functioning as an electrolyte. Typically, the column of gel is pre-polymerized in place in a glass tube or like container. An electric potential is applied to electrodes in contact with the suspension and with the bottom of the column, the suspended particles become charged, and the various types of particles move through the gel at different rates. The separated components thus become concentrated in thin discs at spaced intervals along the gel column. Upon discontinuance of the electric potential, the gel column is removed from the glass tube or other container, and the thin discs are physically separated from one another, as by slicing. Then the individual disc portions are individually reacted with analytical reagents as desired for identification.

Such a technique has been generally described, for example, in U.S. Pat. Nos. 3,384,564 to Ornstein et al., 3,445,360 to Via, and 3,576,727 to Evatt, as well as in Ann. N.Y. Acad. Sci., Vol. 121, at p. 382 and at p. 428 (1964). Unfortunately, such prior disc electrophoresis techniques have been unduly time consuming and often result in at least partial loss of the samples, since the discs must be cut from the gel column after the column has been removed from the glass tube. Also, such prior techniques have not been used to any great extent for determinations of antigenic components of complex mixtures, mainly because the test reactions taking place on a Petri dish outside of the gel column are difficult to observe and read.

It is an object of the present invention to overcome these disadvantages by providing an immunodisc electrophoresis analysis technique for antigenic as well as non-antigenic components of complex mixtures which eliminates the need to remove the gel from the glass tube or other container, and thus avoids the possibility that the gel column may become accidentally broken in an unwanted manner. It is a related object of the invention to provide an immunodisc electrophoresis analytical technique which not only separates and concentrates the components of a test sample into continuous thin discs within an electrophoretic gel column, but which accomodates in situ reactions between the separated component discs and appropriate analytical reagents (e.g. antisera) while the discs are still in place within the column.

A further related object of the invention is to provide such an immunodisc electrophoresis analytical technique in which all of the test reactions may take place within the gel column, i.e. no longer is it necessary to physically separate the component discs from the column and from one another prior to carrying out further treatment of the component discs with analytical reagents. An allied object of the invention is to afford an analyst an analytical tool for studying the antigenic properties of each of the disc components separated in an immunodisc electrophoresis column by observing the results of analytical reactions while the reactants remain inside the column.

Yet another object of the invention is to provide a simple, effective analytical disc electrophoresis technique which yields sharply defined antigenic discs which are easy to count and may readily be reacted in situ with antisera to provide positive sample identification in minimum time.

Other objects and advantages of the present invention will become apparent upon reading the following detailed description and upon reference to the drawings, in which:

FIG. 1 is a perspective view of an illustrative device for preparing an electrophoretic gel column which may be used in carrying out the invention.

FIG. 2 is a perspective view similar to FIG. 1, showing an electrophoretic gel column in place within the preparation device, and a sample to be analyzed in place on top of the gel column.

FIG. 3 is a vertical, sectional schematic view of an illustrative electrophoresis apparatus suitable for use in carrying out the invention, showing the gel column in place within the apparatus.

FIG. 4 is a perspective view of an illustrative larger electrophoresis apparatus for handling a multiplicity of samples simultaneously.

FIG. 5 is an enlarged, diagrammatic vertical cross-section of an illustrative gel column after electrophoresis, showing the various electrophoretically separated components of a sample (in stained condition to render them readily visible).

FIGS. 6, 7 and 8 are enlarged vertical cross-section views of tubes holding illustrative electrophoretic gel columns utilized for different types of analyses carried out in accordance with the invention. FIG. 6 is illustrative of an antigenic analysis, FIG. 7 depicts an enzymatic activity determination, and FIG. 8 is illustrative of use of a developing agent, such as a dye, to stain the electrophoresed components wherever they appear along the column.

While the invention is described in connection with certain preferred embodiments, it will be understood that I do not intend to limit the invention to those embodiments. On the contrary, I intend to cover all alternatives, modifications and equivalents as may be included within the spirit and scope of the invention as defined by the appended claims.

Turning now to the drawings, the illustrative electrophoretic system includes a device 10 for preparing a gel column 11 (FIGS. 1 and 2), and a suitable electrophoresis apparatus 12, shown schematically in FIG. 3, into which the gel column is placed for electrophoresis. If desired, a multiplicity of electrophoresis apparatuses 12 may be operated simultaneously within a larger apparatus 14 (FIG. 4).

With particular reference to FIGS. 1 and 2, it is seen that the illustrative gel preparation device 10 includes a vertically disposed, elongated cylindrical sleeve or tube 15 mounted upon a base 16, which as shown takes the form of a rubber stopper of a type common to analytical laboratories. The rubber stopper 16 carries a cylindrical projection 16a sized to closely fit inside the lower portion of the tube 15, so that a liquid tight seal results when the lower end of the tube has been placed over the stopper projection. The tube 15 is transparent to permit visual inspection of its contents, glass or plastic tubing being preferred materials of construction.

The gel column 11 is prepared by pouring or casting a suitable separating gel, such as polyacrylamide, into the open upper end of the tube 15 until the gel level nears the upper tube end (see FIG. 2). The gel quickly becomes a semi-solid, having pores of various sizes for passing or retaining the different particle sizes present in a given sample.

In carrying out the invention, means is provided for accomodating analytical reactions between electrophoresed components of a sample and selected analytical reagents in situ within the gel column. As shown in the drawings, this is accomplished by forming the gel column as a hollow cylinder, i.e. by providing an elongate central opening or bore 18 passing longitudinally through the gel column 11, the opening providing a repository for analytical reagents added to the column following electrophoresis. In this instance the central opening 18 in the gel column 11 is formed by placing a vertical elongated core rod 19 centrally within the tube 15 prior to casting of the gel. The rod 19 is shown (FIG. 1) mounted upon and supported by the stopper projection 16a, a suitable support recess (not shown) being provided in the stopper for receiving the lower end of the rod. The rod 19 — stopper 16a connection may be screw-threaded or simply a friction fit. Preferably the rod 19 extends beyond the top of the tube 15 to permit ready manual removal of the rod later (see below).

Thus, in preparing the electrophoretic gel column 11, the gel is poured into the tube 15 around the core rod 19 in such a manner that it surrounds the rod. The gel is then allowed to set (polymerize) with the rod in place, so that a cylinder of gel is formed having the vertical rod in its center (see FIG. 2). The gel column 11, tube 15 and rod 19 combination is then separated from the rubber stopper 16 and placed in the electrophoresis apparatus 12. A sample containing antigenic, enzymatic or other components to be analytically determined may then be poured onto the top of the gel column 11, to form a sample layer 20 thereon.

Any of various electrophoretic gels may be used with the invention, for example polyacrylamide, agar, starch, pectin, sephadex, cellulose, or any other substance which in aqueous or organic fluids forms a clear, transparent, translucent, or colored gel and which is capable of being packed to a semi-solid condition to form a gel cylinder. The gel cylinder may be cast in tubes of various lengths and diameters as desired. The casting can be carried out while the tube 15 is in a vertical or horizontal position, either manually, using pressure, or by vacuum operated casting devices. While the base 16 for the gel preparation device is shown as a rubber stopper, other base materials such as a screw cap or plastic closure may be used as well. The core rod 19 may be formed of glass, plastic or metal, should have a diameter smaller than the inside diameter of the tube 15, and should be of sufficient length to facilitate its later manual removal from the tube.

As will be seen from FIG. 3, the electrophoresis is carried out with the rod 19 in place within the tube 15. The electrophoresis apparatus 12 includes a suitable support structure (not shown) for mounting the gel tube 15, column 11 and embedded rod 19 between upper and lower reservoirs 21, 22, respectively. A source of electric current 24 is provided, suitably connected to positive and negative electrodes 25, 26 disposed in the upper and lower reservoirs, respectively, and the reservoirs are filled with appropriate buffer solutions 28, 29 of a type well known to those skilled in the art.

Upon application of electric potential to the electrodes 25, 26, electrophoresis takes place, with the suspended particles in the sample layer 20 becoming electrically charged and moving downwardly through the gel column 11 at different rates of travel depending upon their nature. The gel containing tube 15 is left in this position in the electrophoresis apparatus 12 for whatever length of time is necessary for the components of the sample to migrate from the top of the gel column 11 downwardly to various longitudinally spaced positions within the gel. After the desired time of electrophoresis has elapsed, the tube 15, gel column 11 and rod 19 are disengaged from the source of electric current and the central rod 19 is removed manually from the gel column. At this point the gel column 11, which is hollow by reason of its central bore or lumen 18, has the annular or hollow cylinder appearance depicted in FIG. 5. The sample components have been completely separated from each other along the column, and appear as a plurality of individual discs 30.

In the event that the larger electrophoresis apparatus of FIG. 4 is used for simultaneous preparation of multiple samples, the operation is like that described above as concerns FIG. 3. Thus, the larger apparatus 14 includes upper and lower reservoirs containing buffer solutions 28a, 29a into which the ends of a plurality of gel tubes 15a are immersed. The gel tubes 15a include central rods 19a, with sample layers 20a being present at the beginning of electrophoresis. Electric current is supplied to the larger electrophoresis apparatus through electrodes 25a, 26a.

Following electrophoresis to separate the components of the sample into discs spaced along the gel column, the bore or lumen 18 of the column may be filled with any desired analytical reagent, and the column incubated, whereupon localized test reactions may be caused to take place at the locale of each disc. For example, analytical reagents used may include antisera, stain or a suitable substrate, or combinations thereof, depending upon the nature of the analytical determination being carried out. Importantly, the analytical procedure avoids the necessity for removing the gel column 11 from the tube 15.

FIGS. 6, 7 and 8 depict several ways in which the present invention may be utilized in conducting analytical determinations. The illustrative of FIG. 6 relates to determination of the antigenic components of a sample. Following electrophoresis of the separate antigenic components into discs spaced along the gel column 11, the tube 15 and gel column are removed from the electrophoresis apparatus and placed in a horizontal position. Then the bore or lumen 18 of the gel cylinder is filled with antiserum containing antibodies to all or some of the antigenic components of the sample. Alternatively, the antiserum may be premixed with a gelling agent, such as agar, so that after being placed in the cylinder it forms an inner gel and serves as a repository for the antiserum. The tube 15 is then suitably sealed at both ends to prevent evaporation, e.g. with plastic film, and the antigen-antibody reaction is allowed to take place by incubating the tube at the desired temperature. The antigen-antibody reaction results in precipitation which appears as white bands 31 either in the outer gel column or in the inner gel, and the test results are read as such.

FIG. 7 depicts the results of a determination of the enzymatic components of a sample. Following electrophoretic separation of the individual enzymatic components into discs spaced along the column 11, the cylinder bore 18 is filled with the substrate of the enzyme whose activity, location, and number is being analyzed. The substrate may be premixed with any necessary indicator system for detecting enzymatic activity, or the substrate and indicator system may be mixed with a gelling agent before being placed in the bore. The gel cylinder filled with these agents is then incubated at the desired temperature and the location of the particular enzymes noted from the presence of pockets 32 of precipitate.

Alternatively, the hollow gel cylinder 11 may be filled with a developing agent, such as a dye, which will stain the sample components wherever they may be located in the gel. In this event, the cylinder bore 18 is filled with a stain or other developing agent, and the agent is allowed to remain within the bore until the components of the sample have been stained or have otherwise become altered so that they may be observed (see the bands 34 of FIG. 8). The excess stain or the agent is then removed by filling the cylinder bore with washing solution of a composition compatible with the stain or other reagent used.

It will thus be seen that the invention may be utilized in the analysis of antigenic as well as non-antigenic components of biological and other fluids and extracts. For example, the improvements described herein may be used in the analysis of enzymatic, hemolytic, and toxic components of such fluids and extracts. Moreover, the advantages and objects of the invention may be attained in various ways. By utilizing the invention, an analyst may study the enzymatic properties of electrophoretically separated sample components by reacting them with an appropriate substrate disposed in the hollow portion of the gel column. The enzyme-substrate reactions may be visualized, if necessary, through use of indicators present in the substrate or applied separately after the enzymatic reactions have altered the substrate.

The invention advantageously also may be used in studying different forms of isoenzymes, either by serological or biochemical reactions taking place within the gel column.

I claim as my invention:

1. Apparatus for carrying out analytical determinations on a sample containing unknown components, comprising, in combination, a hollow enclosure, an electrophoretic gel column within said enclosure and adapted to receive the sample at one end thereof, means for electrophoretically separating the various components of the sample from each other and disposing them across the gel column at intervals therealong, said gel column having a central bore therein open for receiving an analytical reagent for contacting the separated components of the sample disposed along the column.

2. A device for carrying out analytical determinations on a sample containing unknown components, comprising, in combination, an elongated container, an elongated electrophoretic gel disposed in said container, and means for separating the components of the sample into concentrated discs spaced along said gel, said gel having a central bore therein open for receiving an analytical reagent for contacting the separated components of the sample and having an axis coincidental with that of said container.

3. Apparatus for use in electrophoresis and electrofocusing including a hollow transparent elongated enclosure and an elongated core member of smaller cross-section than the cross-section of the enclosure within the enclosure, stopper means for closing one end of said enclosure, said stopper means removably holding said member in a selected position within said enclosure, and a separating gel in said enclosure and between said core member and enclosure.

4. The structure of claim 3 wherein said enclosure is a tube and said member is a rod.

5. The structure of claim 4 wherein said stopper means include means for holding said rod coaxially with said tube.

6. The structure of claim 3 wherein said enclosure has an annular cross-section.

* * * * *